United States Patent [19]

Rosenberg et al.

[11] 4,059,688

[45] Nov. 22, 1977

[54] HAIR FIXING COMPOSITIONS CONTAINING FLUOROTERPOLYMERS AND METHOD

[75] Inventors: Ira E. Rosenberg, West Norwalk; John A. Ferguson, Darien; Norman P. Loveless, Fairfield, all of Conn.

[73] Assignee: Clairol Incorporated, New York, N.Y.

[21] Appl. No.: 701,006

[22] Filed: June 29, 1976

[51] Int. Cl.$^2$ .............................................. A61K 7/11
[52] U.S. Cl. .................... 424/71; 8/127.51; 132/7; 260/29.6 F; 260/29.6 ME; 260/29.6 MN; 260/29.6 T; 260/29.6 TA; 424/DIG. 1; 424/DIG. 2; 424/47; 424/81
[58] Field of Search ............ 260/29.6 F, 29.6 T, 260/29.6 TA, 29.6 MN, 29.6 ME; 424/DIG. 1, DIG. 2, 47, 71, 81; 8/127.51; 132/7; 520/245

[56] References Cited

U.S. PATENT DOCUMENTS

| | | | |
|---|---|---|---|
| 3,378,609 | 4/1968 | Fasick et al. | 260/29.6 F |
| 3,462,296 | 8/1969 | Raynolds et al. | 260/29.6 T |
| 3,491,169 | 1/1970 | Raynolds et al. | 260/29.6 F |
| 3,617,165 | 11/1971 | Kalopissis | 8/10.1 |
| 3,645,989 | 2/1972 | Tandy | 260/29.6 F |
| 3,657,173 | 4/1972 | Eanzel et al. | 260/29.6 F |
| 3,721,655 | 3/1973 | Schlumbom et al. | 424/70 X |
| 3,822,228 | 7/1974 | Petrella et al. | 260/29.6 F |
| 3,850,178 | 11/1974 | Schoenholz | 132/7 |
| 3,922,341 | 11/1975 | Abegg et al. | 424/47 |
| 3,927,199 | 12/1975 | Micchelli et al. | 424/47 |
| 3,932,614 | 1/1976 | Scott | 424/78 |
| 3,934,595 | 1/1976 | Madrange et al. | 132/7 |
| 3,959,462 | 5/1976 | Parks et al. | 424/70 |
| 3,972,998 | 8/1976 | Keiner | 424/70 |
| 3,984,536 | 10/1976 | Viout et al. | 424/47 |
| 3,993,745 | 11/1976 | Cella et al. | 424/71 |
| B 464,491 | 3/1976 | Pavlik et al. | 132/7 |

FOREIGN PATENT DOCUMENTS

| | | | |
|---|---|---|---|
| 940,049 | 1/1974 | Canada | 424/70 |

*Primary Examiner*—Albert T. Meyers
*Assistant Examiner*—Vera C. Clarke
*Attorney, Agent, or Firm*—Irving Holtzman; George A. Mentis; David J. Mugford

[57] ABSTRACT

Hair fixation with fluorine containing acrylate or methacrylate terpolymers or with mixtures thereof with known non-fluorine containing hair fixing polymers.

18 Claims, No Drawings

HAIR FIXING COMPOSITIONS CONTAINING FLUOROTERPOLYMERS AND METHOD

This invention relates to compositions and methods for the fixation of hair. More particularly, it concerns the use of certain polymeric compositions for these purposes which give improved results, especially with respect to curl or wave retention and hair feel.

A great variety of hair fixing (including styling, controlling, wave setting, curl setting, straightening, etc.) compositions have been proposed and/or marketed which contain a resinous or polymeric binder material intended to be deposited as a thin film or coating on the hair to thereby fix, set or hold the hair in any desired shape or configuration. Such compositions should ideally possess a combination of several properties which are often difficult to attain and which may in some instances be mutually opposed. For example, although the treated shaped hair should be sufficiently water insensitive or non-hygroscopic to avoid humidity degradation, development of tackiness, loss of holding power, etc. on exposure to relatively humid conditions, the film on the hair should be sufficiently water sensitive to be readily removable when so desired by treatment with water, soap and/or shampoo. In addition, although the treated hair should have good holding power, e.g., have good curl retention properties, it should not give the hair a "boardy" or unnatural feel.

It has now been found that good hair fixing and curl retention properties may be imparted to hair by treating the hair with a composition containing certain fluoroterpolymers described in more detail below. This can be accomplished with such compositions without giving the hair a "boardy" feel and without sacrificing the readiness with which these compositions may be washed out of the hair. It has further been found that the hair fixing or curl retention properties of these fluoroterpolymer containing compositions may further be enhanced if there is also included in said compositions a film forming resin such as those now conventionally employed in hair fixing compositions.

Other desirable and/or necessary properties for hair fixing compositions include stability and clarity in storage of the composition or its components; pleasing appearance, compatibility, good solubility in organic solvents and aerosol propellants, ease of application such as sufficient fluidity, etc. The films deposited therefrom should have good antistatic properties, clarity, transparency (water white or colored), sheen, substantivity or adhesion to the hair, resistance to flaking, ease of combing and brushing, and, of course, good holding properties under varying conditions of wind, weather, and mechanical contact and agitation. The compositions of this invention seek also to provide these properties.

It is accordingly an object of this invention to provide hair fixing compositions which will not be subject to one or more of the disadvantages outlined above.

Another object of this invention is the provision of such compositions possessing an increased number or proportion of the above discussed desirable properties.

Still another object of this invention is the provision of such compositions having improved curl or wave retention properties especially under humid conditions.

A still further object of the present invention is to provide a composition having improved curl or wave retention properties and yet when applied leave the hair with a soft feel.

Yet another object of this invention is the provision of hair fixing compositions in which fluoroterpolymers of improved vehicle solubility properties are employed.

Further objects of this invention are the provision of hair fixing methods employing compositions set forth in the above objects.

Other and more detailed objects and advantages will appear from the following description and claims.

The fluoroterpolymers that are useful in formulating the hair fixing compositions of the present invention are terpolymers of (a) at least one fluoroalkanol ester of acrylic or alkyl acrylic acid e.g. methacrylic acid, (b) at least one ester of acrylic or an alkyl acrylic acid with a polyoxyalkylated alkanol ether of an alkyl phenol, and (c) at least one bis-alkylaminoalkyl acrylate or alkylacrylate (e.g. methacrylate) or the N-oxide or quaternary amine salts thereof. More particularly, the terpolymers will be comprised of the following monomeric mixture, the percentages being given as approximate percentages by weight:

a. 60–85% (preferably 70–75%) of at least one ester of the formula:

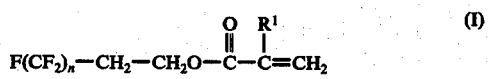

in which:
1. $n$ is a number having an average value of from 3 to 20 and preferably from 5 to 15; and
2. $R^1$ is hydrogen or lower alkyl from 1 to 4 carbons e.g. methyl, ethyl, n-propyl, i-propyl, n-butyl (preferably methyl);

b. 10–30% (preferably 20–25%) of an ester of the formula:

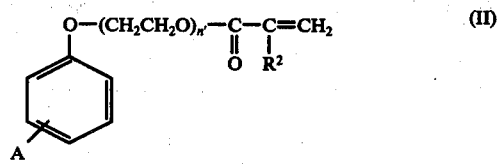

in which:
1. A is alkyl having 5 to 15 carbons (preferably octyl, nonyl);
2. $n'$ is a whole number having an average value of about from 20 to 45 (preferably 37); and
3. $R^2$ is hydrogen or lower alkyl from 1 to 4 carbons e.g. methyl, ethyl, n-propyl, i-propyl, n-butyl (preferably methyl);

c. 2–10% (preferably 50%) of an amine ester of the formula:

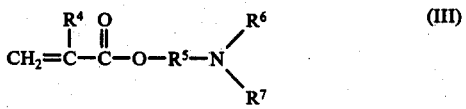

or the
N-oxide or a quaternary amine salt thereof in which:
1. $R^4$ is hydrogen or lower alkyl having 1 to 4 carbons e.g. methyl, ethyl, n-propyl, i-propyl, n-butyl (preferably methyl);
2. $R^5$ is a divalent straight chain or branched chain aliphatic hydrocarbon radical having 1 to 6 carbons, preferably 2 carbons e.g. —CH$_2$—, —CH$_2$—CH$_2$—,

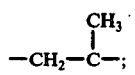

—CH$_2$—CH$_2$—; —CH$_2$CH$_2$—CH$_2$—CH$_2$—, etc.

3. R$^6$ and R$^7$ are lower alkyl having from 1 to 4 carbon atoms e.g. methyl, ethyl, n-propyl, i-propyl, n-butyl. These polymers will usually have a molecular weight of the order of 10$^3$ to 10$^6$ and preferably about 10,000 to 20,000.

As indicated above, the amine ester of formula III may be employed as the N-oxide or as a quaternary amine salt. The amine oxides can be prepared from the corresponding tertiary amines by conventional methods such as by oxidation with aqueous hydrogen peroxide (see "Organic Chemistry" 3rd Edition, by Fieser and Fieser, Reinhold Publishing Corp. New York, 1956, pages 239-240).

Similarly when the amine ester of formula III is used in the form of the quanternary amine salt, any of the conventional quaternizing agents may be used to form the quaternary compound employed. As illustrative of such quaternizing agents, there may be mentioned alkyl halides such as methyl, ethyl, n-propyl, i-propyl, n-butyl and butyl bromide, chloride and iodide; dialkyl sulfates such as dimethyl and diethylsulfate; 2-bromoethanol, beta-propiolactone, 1,3-propane sulfone; benzyl halide such as benzyl chloride, bromide and iodide; alkyl sulfonates such as ethyl p-toluenesulfonate and methyl xylene sulfonate and the like and mixtures thereof.

The above described fluoroterpolymers have improved solubility characteristics in the liquid vehicle ordinarily employed in hair fixing compositions. Moreover, they give hair treated therewith improved curl, wave or shape retention properties especially under relatively high humidity, and improve the feel of the hair. They can accordingly be used to advantage as, essentially, the sole polymeric material in the hair fixing compositions. However, for certain purposes, the capabilities of these compositions may be greatly improved by also incorporating in the composition a non-fluorine containing polymer, particularly those of the film forming type that are known in the art to serve as hair fixing polymers.

However, where the fluoroterpolymer is used in conjunction with other hair fixing polymers, the former will usually be present in the range of from about 0.01% to 2% by weight based on the total weight of the composition.

As pointed out above, the fluoropolymers of the present invention are terpolymers made from three monomers described by general formulas I, II and III above. By way of further illustrating particular fluoroterpolymers that are useful in the present invention, the following are given. These will have a M.W. of the order of about 10,000 to 20,000. The monomers in said polymers are defined as follows:

MONOMER A

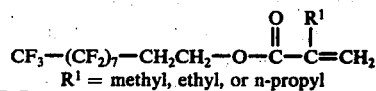

$R^1$ = methyl, ethyl, or n-propyl

MONOMER B

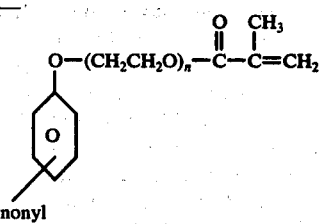

n = 30, 35 or 37

MONOMER C

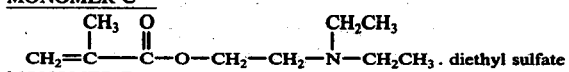

. diethyl sulfate

MONOMER D

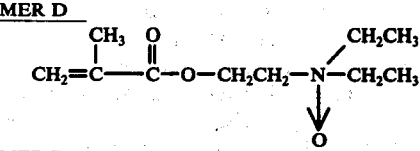

MONOMER E

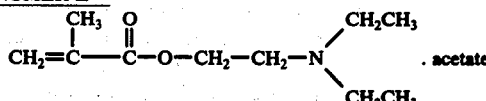

. acetate

MONOMER F

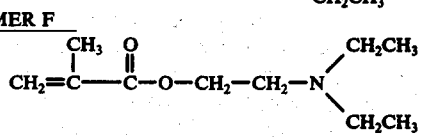

| | | FLUOROTERPOLYMERS | | | | | |
|---|---|---|---|---|---|---|---|
| Ex. (a) | Monomer A | (R$^1$=ethyl) [70%] | Monomer B | (n=30) | [25%] | Monomer C | [5%] |
| Ex. (b) | " | (R$^1$=n-propyl) [70%] | " | " | " | " | " |
| Ex. (c) | " | (R$^1$=n-propyl) [70%] | " | (n=35) | " | " | " |
| Ex. (d) | " | (R$^1$=n-propyl) [75%] | " | " | [20%] | " | " |
| Ex. (e) | " | (R$^1$=methyl) [75%] | " | (n=37) | [20%] | Monomer D | [5%] |
| Ex. (f) | " | (R$^1$=methyl) [70%] | " | (n=37) | [25%] | " | " |
| Ex. (g) | " | (R$^1$=methyl) [75%] | " | (n=37) | [20%] | Monomer E | [5%] |
| Ex. (h) | " | (R$^1$=methyl) [70%] | " | (n=37) | [25%] | " | " |
| Ex. (i) | " | (R$^1$=methyl) [75%] | " | (n=37) | [20%] | Monomer F | [5%] |
| Ex. (j) | " | (R$^1$=methyl) [70%] | " | (n=37) | [25%] | " | " |

The quantity of fluoroterpolymer that will be contained in the compositions of the present invention may vary depending upon the results desired (e.g. the softness of the feel, strength of curl retention) and/or the type and quantity of the other components of the composition and particularly, the quantity of non-fluorine containing hair fixing polymer. In general, however and from a broad point of view, the quantity of fluoroterpolymer (as 100% fluoroterpolymer) will comprise from about 0.01 to 10% (and preferably .2% to 5%) by weight based on the total weight of the composition.

The above described fluoroterpolymers may be made by several processes well known to those skilled in the polymer art. For example, they are prepared by aqueous emulsion polymerization using free radical initiation. Any known system for aqueous emulsion polymerization of water insoluble methacrylate esters may be used. In general, any free radical initiator may be used such as organic or inorganic peroxides or organic aliphatic azo compounds. Broadly, either cationic or anionic emulsifying agents may be used in the polymerization but nonionic agents are generally avoided. The cationic agents are preferred, particularly salts of long chain tertiary alkyl amines.

A preferred method for preparing the fluorinated terpolymers employed in this invention involves pre-emulsification of the water insoluble monomers, using dimethyloctadecylamine acetate as the dispersing agent, and then combining this emulsion with a water solution of the water soluble monomers, azo initiator and a mercaptan chain modifier, preferably dodecyl mercaptan. From 0.03% to 0.1% by weight on total weight of monomers of dodecyl mercaptan is used. The preferred initiator is azo bis(isobutyramidine)dihydrochloride. The total monomer content in the preferred aqueous emulsion polymerization process is about 25% by weight.

The polymerization temperature, which naturally varies with the initiator being used, may vary from 40° C to as high as 130° C if autogeneous pressure is used. The preferred azo catalyst above requires about 65° C. Higher temperatures can be attained using inorganic peroxides such as potassium persulfate, peroxyanhydrides such as benzoyl peroxide, peroxy esters, such as tert-butyl perbenzoate or ditertiary alkyl peroxides such as ditert-butyl peroxide.

When the fluorinated terpolymer contains more than 80% of the fluorinated monomer, it is preferred to use a different polymerization system, an aqueous dispersion polymerization system. This process is identical to that described in the previous paragraphs except that a water insoluble azo initiator, preferably azo bis(isobutyronitrile), is used. Polymerization temperatures and times are essentially the same as for the earlier process. While preferred for polymers containing more than 80% of the fluorinated monomer, this process may be used to prepare any of the fluorinated polymers employed in this invention.

It is also a feature of the present invention to include a non-fluorine containing secondary hair fixing polymer in the instant compositions. Any of a large variety of film forming polymers that are well known in this art that are suitable as hair fixing agents can be employed. These may be homopolymers, copolymers of two or more monomers, graft copolymers. Moreover, they may be non-ionic, cationic or anionic.

The monomers that may be employed in forming the non-fluorine containing secondary hair fixing polymers used in this invention can vary widely. Ordinarily, they will fall into one or more of the following general categories:

A. olefinic acids or esters

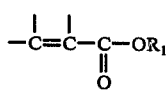

wherein $R_1$ is hydrogen or an organic radical.

B. olefinic ethers

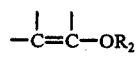

wherein $R_2$ is an organic radical.

C. olefinic acid amides

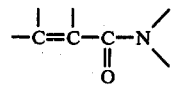

D. olefins

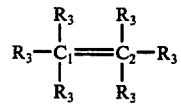

wherein $R_3$ is hydrogen, the same or different monovalent organo group bonded to carbon $C_1$ or $C_2$ through a carbon of $R_3$.

E. olefinic acid anhydrides

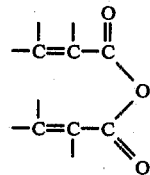

Although any combination of fluoroterpolymers with said secondary film forming hair fixing polymer may be employed, it has been found that when a non-ionic type fluoroterpolymer is employed, it is advantageous to also use as the secondary polymer one which is also non-ionic or one which is highly neutralized at least 51%. Commonly when an ionic fluoroterpolymer is selected for use, it is beneficial to also employ as a secondary polymer one which is ionic or one which is neutralized only to a lesser degree (e.g. 0 to 50%). With these combinations the best increase in curl retention appears to be obtained.

The above has been demonstrated by measuring the curl retention in an atmosphere of 90% relative humidity of curls treated with a composition containing a non-ionic type fluoroterpolymer and a highly neutralized secondary polymer (e.g. Amphomer or Resyn 28-1310, 90% neutralized) or a non-ionic secondary polymer (e.g. PVP or VP/vinyl Acetate copolymer). With this combination, the greatest increase in curl retention is obtained with a non-ionic fluoroterpolymer. On the other hand, when an ionic fluoroterpolymer is selected, the greatest increase in curl retention is obtained when the secondary polymer is only partially neutralized (e.g. Gantrez ES 425, 20% neutralized or Gantrez ES 225 10% neutralized).

The exact mechanism that would explain the synergy achieved between the fluoroterpolymer and the secondary hair fixing polymer in increasing the curl retention characteristics, in accordance with the present invention, is not clearly understood. The evidence, however, seems to indicate it may be due to the fact that the polymer film that is laid down on the hair is a homogeneous solid solution of both the fluoroterpolymer and the secondary polymer and that a coupling or associative process probably occurs between the fluoroterpolymer and the secondary polymer. This postulation is supported by the observation that the more alike the chemical character of the fluoroterpolymer and secondary polymer, the greater the curl retention characteristics of the composition. This is consistent with chemical adage that like materials tend to be mutually soluble;

whereas, unlike materials tend to be insoluble in each other.

This postulaton is also supported by certain physical measurements which were made. Thus, multiple internal reflectance infrared spectroscopy was used to examine air dried films of Amphomer and Gantrez ES 425 resin. Spectra were recorded for both sides of the resin films i.e. front side exposed to air and back side cured in contact with a polyethylene laminate. Fluoroterpolymers were then incorporated into the Amphomer and Gantrez formulations. Air dried films of the fluoroterpolymer formulations were re-examined for spectral differences.

No differences in spectral characteristics were observed between the various fluoroterpolymers in the resin films. Since the internal reflectance technique is essentially a surface measurement, it is concluded the fluoroterpolymers do not preferentially migrate to the air/solid interface. The fact that no spectral differences were observed, would indicate that the fluoroterpolymers are homogeneously dispersed in the resin films.

One of the unique features of this invention is the fact that set hold of hair fixatives can now be controlled by two variables according to the following relationship:

$$\text{Set Hold} = \text{Concentration of Fluoroterpolymer} + \text{Concentration of Secondary Polymer}$$

This relationship allows the formulator to choose a desired level of set hold and then vary both the fluoroterpolymer and secondary polymer content to achieve the desired cosmetic effect.

In selecting the quantity of secondary polymer to be incorporated in the composition of the present invention, the formulator will be governed by the above described relationship between fluoroterpolymer and secondary polymer. If, for example, a softer "feel" is required in hair treated with these compositions, the formulator could reduce the quantity of secondary polymer and increase the quantity of fluoroterpolymer. In general, however, the quantity of secondary polymer contained in the composition of this invention will be in the range of from about 0.5% to about 10% by weight (and preferably between about 2% to 5%) based on the total weight of the composition.

As indicated above, any known non-fluorine containing film forming hair fixing polymer may be employed as the secondary polymer in the compositions of this invention. These may be devoid of replaceable groups or moieties (e.g. ionizable group), or may contain varying proportions of such groups such as the reactive hydrogen in hydroxyl, primary or secondary amino or carboxyl. When polymers containing such groups are employed, such groups are preferably but not necessarily acidic, i.e. carboxyl.

As suitable non-fluorine containing secondary polymers, there may be mentioned those containing replaceable groups (e.g. ionizable groups). Those preferred contain pendant carboxyl groups as derived, for example, from one or more olefinically unsaturated carboxylic acids i.e. monolefinic and polyolefinic monocarboxylic and polycarboxylic acids, preferably containing an olefinic bond in alpha-beta relation to a carboxyl group or attached to a terminal methylene group, by homopolymerization or copolymerization with one or more other copolymerizable olefinically unsaturated monomers.

As illustrative of such unsaturated carboxylic acids, there may be mentioned acrylic, methacrylic, chloroacrylic, maleic, fumaric, crotonic, itaconic, angelic, cinnamic, sorbic, beta-(2-butene) acrylic, 2,4,6,8-decatetraenoic, alpha vinyl cinnamic, hydromuconic, glutaconic, 3-carboxy-pentadiene-(2,4)-oic-1, muconic, alpha and beta vinyl acrylic partial esters of unsaturated polycaboxylic acids e.g. maleic acid or anhydride half esterified with $C_{1-4}$ alkanols or oxyalkylenated derivatives (such as with ethylene oxide) derivatives of such alkanols, and the like, and inert substituted derivatives thereof.

As other copolymerizable olefinically unsaturated monomers copolymerizable with the above mentioned unsaturated carboxylic acids to form said secondary polymers that are useful herein, there may be mentioned the amides and $C_{1-18}$ alkyl and hydroxyalkyl esters of acrylic and methacrylic acids such as the methyl and hydroxy stearyl acrylates and methacrylates, acrylamide, N-dodecylacrylamide, and N,N-dimethylmethacrylamide, the vinyl esters and amides of $C_{2-18}$ saturated aliphatic monocarboxylic acids such as vinyl acetate, stearate, and 2,2,4,4-tetramethyl valerate, $C_{1-18}$ alkyl vinyl ethers such as methyl isopropyl and stearyl vinyl ether, styrene, vinylidene chloride, olefins such as ethylene propylene and isobutylene, N,N-$(C_{1-4})$alkylamino, $C_{(2-4)}$alkyl esters and amides of acrylic and methacrylic acid such as N,N-diethylaminoethyl methacrylamide and methacrylate and N,N-dimethylamino isopropyl acrylamide and acrylate vinyl pyridine, vinyl imidazole, N-vinyl pyrrolidone, quaternary ammonium derivatives of any of the foregoing monomers containing a basic tertiary nitrogen atom and the like.

As suitable secondary non-fluorine containing polymers, devoid of replaceable (e.g. ionizable) groups, polymerization products of most or all of the "copolymerizable olefinically unsaturated monomers" described in the previous paragraph, as homopolymers or copolymers from two or more such monomers may be employed in the compositions of this invention, in combination with the described fluoroterpolymers.

The following are more specific examples of more readily available non-fluorine containing hair fixing polymers which may be employed in the compositions of this invention as the secondary polymer. It is to be understood that any other such polymers may be similarly employed:

| | Polymers with Replaceable or Ionizable Groups |
|---|---|
| Gantrez AN 119 | (maleic anhydride/methyl vinyl ether |
| Gantrez AN 139 | copolymer, GAF Corp.; at least partially |
| Gantrez AN 169 | hydrolyzed) |
| Gantrez ES 225 | (monoethyl ester of maleic anhydride/methyl vinyl ether copolymer, GAF Corp.) |
| Gantrez ES 325 | (monopropyl ester of maleic anhydride/methyl vinyl ether copolymer, GAF Corp.) |
| Gantrez ES 425 | (monobutyl ester of maleic anhydride/methyl vinyl ether copolymer, GAF Corp.) |
| Resyn 28-1310 | (vinyl acetate/crotonic acid copolymer, National Starch & Chemical Corp.) |
| Resyn 28-2930 | (vinyl acetate/crotonic acid/vinyl neodecanoate terpolymer, National Starch & Chemical Corp.) |
| EMA 11 | (ethylene/maleic anhydride copolymer, Monsanto Corp.) |
| | Polymers with Little or No Replaceable Groups |
| Amphomer | (90% neutralized with AMP i.e. 2-amino-2-methyl-1-propanol) amphoteric terpolymer/acrylamide/acrylates/butylamino-ethyl methacrylate polymer containing neutralizable carboxy groups |
| Resyn 28-1310 | (90% neutralized with AMP) vinyl acetate/crotonic acid copolymer |
| PVP | (polyvinyl pyrrolidone, GAF Corp.) |

-continued

| Polymers with Replaceable or Ionizable Groups |
| --- |
| PVP/VA (vinyl pyrrolidone/vinyl acetate copolymer, GAF Corp.) |
| Dicrylan 325-50 (acrylate/acrylamide copolymer, Ciba Geigy) |
| Dicrylan 394 (acrylate/acrylamide copolymer, Ciba Geigy) |

The molecular weights of the polymers employed in accordance with this invention are not critical and may range for example, from about 5,000 to 2,000,000, preferably about 10,000 to 300,000. All that is required is that they be film forming and sufficiently dispersible or preferably soluble to the desired concentration in the liquid medium in which they are contained.

The composition of the present invention will ordinarily comprise a vehicle containing the fluoroterpolymer and the so-called secondary hair fixing polymer. These polymers may be incorporated in a solvent system or some other liquid system in the form of a true solution, a dispersion, an emulsion or a lotion. Moreover, they may be incorporated in a cream, gel or foam base or incorporated in an aerosol propellant system. These compositions may also include other adjuvants or assistants that are useful in preparing cosmetically elegant products or imparting other useful properties to the hair. By way of illustrating the other adjuvants that may also be incorporated in the present composition, the following is given: coupling agents, plasticizers, emollients, thickeners, lubricants, penetrants, buffering agents, surfactants, dyes and other colorants, preservatives, medicaments, UV absorbers, perfumes, protein hydrolyzates and other protein derivatives, brilliance modifiers, conditioners, anti-static agents, anti-hygroscopic agents, clarifiers, evaporation accelerators, foaming or defoaming agents, and the like. These when present will generally be present in relatively low proportion e.g. from about 0.1 to 5% by weight based on the weight of the composition.

When the composition takes the form of an aerosol product, any of the known aerosol propellants may be used in formulating the product. For example, the propellant may be gaseous such as carbon dioxide, nitrous oxide or nitrogen or mixtures thereof, or one or a mixture of liquified normally gaseous propellants including hydrocarbons such as propane, n-butane and isobutane and low boiling halohydrocarbons such as methylene chloride, 1,1,1-trichloroethane, and the fluorinated hydrocarbon generally available variously under the designations "Freon" (E. I. DuPont), "Genetron" (Allied Chemical), and "Isotron" (Pennwalt Chemical). Illustrative of the latter types are trichloromonofluoromethane, dichlorodifluoromethane; dichlorotetrafluoroethane, 1-chloro-1,1-difluoroethane, 1,1-difluoroethane, monobromomonochlorodifluoromethane and the like. Mixtures of gaseous and liquified normally gaseous propellants may also be employed such as trichlorofluoromethane and about 2 to 10% by weight of nitrous oxide.

When the product takes the form of an aerosol product, the actives i.e. the fluoroterpolymer or the mixture of fluoroterpolymer and secondary polymer may be added as such to the propellant or may be added as a concentrate in a liquid or solvent system. In this case, the propellant will comprise between about 20 to 90% by weight based on the total weight of the composition; the balance being made up by the actives or the concentrate containing the actives.

In the preferred form of the invention, the vehicle employed is a solvent system in which the fluoroterpolymer and secondary polymer are soluble. The solvent system may comprise a single solvent or a combination of solvents. They will ordinarily be organic solvents preferably those which are volatile and may also be water or aqueous organic solvent systems. Typical solvents that may be employed for these purposes included the lower alkanols e.g. containing 2 to 4 carbons e.g. ethanol, n-propanol, isopropanol; hydroalcoholic solvents (e.g. ethanol-water); ester solvents such as ethyl acetate, amyl acetate; halogenated hydrocarbons (e.g. methylene chloride, Freon 11, Freon 114).

In some instances, where some of the secondary polymers employed are unneutralized, or only partially neutralized, it may be advantageous to add an additional base to at least partially neutralize the secondary polymer. This may be added to an extent up to complete neutralization of the secondary polymer. This may be accomplished as a separate step or the base may be added to the composition containing fluoroterpolymer and at least a partially unneutralized secondary polymer. The neutralizing agent employed may be any inorganic or organic base or alkaline material and may be applied prior to or after combination with the fluoroterpolymers. As illustrative of such agents, there may be mentioned alkali metal hydroxide such as sodium and potassium hydroxide, primary, secondary and tertiary amines such as di- and tri- methyl, -ethyl and -isopropyl amines and isobutyl amine, alkanolamines such as triethanolamine, triisopropanolamine, 2-amino-2-methyl-1-propanol and 2-amino-2-methyl-1,3-propanediol, and volatile bases such as ammonia, ammonium carbonate, mono lower alkylamines including monomethyl, -ethyl and -isopropyl amines and mixtures thereof.

As noted above, a primary feature of the compositions of the present invention is that they may be employed in fixing hair. When used for this purpose, the compositions may be applied to the hair prior to or simultaneously with the hair shaping step, and the wetted hair dried in situ while held in the desired shape configuration. Enough of the compositions may be applied to the hair to saturate it. Alternatively (or in addition) said compositions may be applied to the hair while it is constrained in its desired shape configuration and the wetted hair may be similarly dried in situ while so constrained. Conventional hair driers or similar blowing and/or heating devices are preferably employed to hasten the drying time and accelerate the curing of the polymer. This process may be carried out on the human head or it may be used to fashion the hair in a wig.

The following Examples are given to further illustrate the present invention. It is to be understood, however, that this is not to be regarded as limitative. All amounts and proportions referred to herein and in the appended claims are by weight unless otherwise specified.

The following expressions have the meanings ascribed to them below wherever used herein:

1. FND-N-oxide 75/20/5

A terpolymer (M.W. about 10,000 to 20,000) containing 75% of a mixture of compounds of formula:

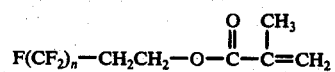

wherein n is 6, 8 and 10 in the weight ratio of 3:2:1 and less than 10% by weight of compounds in which n = 12 and 14; 20% of

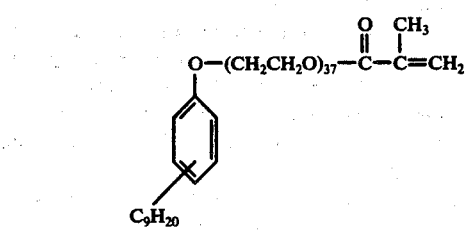

and

5% of

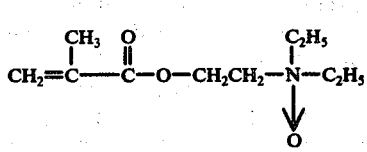

2. FND 70/25/5

A terpolymer containing 70% of a mixture of compounds of formula:

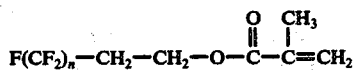

wherein n is 6, 8 and 10 in the ratio of 3:2:1 and less than 10% by weight of compounds wherein n = 12 and 14; 25% of

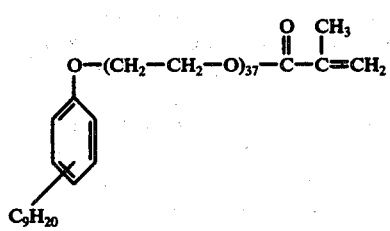

and

5% of

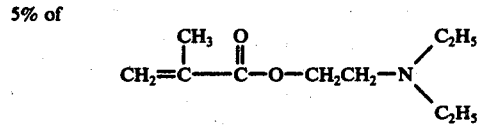

AMP: 2-amino-2-methyl-1-propanol

Amphomer: (An amphoteric terpolymer) acrylamide/acrylates/butylamino-ethyl methacrylate polymer containing neutralizable carboxy groups Resyn 28-1310: Vinyl acetate/crotonic acid copolymer; intrinsic viscosity 0.32 measured in acetone at 30° C Gantrez ES 425: Monobutyl partial ester of poly (methyl vinyl ether/maleic acid)

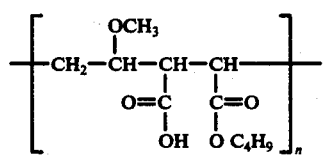

molecular weight about 250,000

PVP: Linear polymer of 1-vinyl-2-pyrrolidone

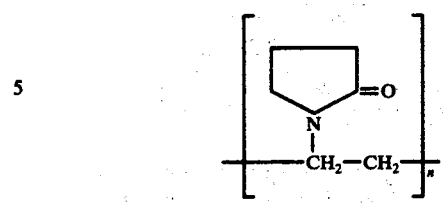

PVP/VA E-735: Copolymer of vinyl acetate (30%) and vinyl pyrrolidone (70%)

The following ingredients were mixed together in the quantities indicated to give products in the form of solution that are useful for hair fixing in accordance with the present invention.

TABLE I

| Material | % by Weight | | | | | | |
|---|---|---|---|---|---|---|---|
| | Ex. 1 | Ex. 2 | Ex. 3 | Ex. 4 | Ex. 5 | Ex. 6 | Ex. 7 |
| Deionized H₂O | 6.6 | 6.6 | 6.6 | 6.6 | 6.6 | 6.6 | 66.6 |
| Isopropanol | 2.3 | 2.3 | 2.3 | 2.3 | 2.3 | 2.3 | 2.3 |
| AMP | 0.4 | 0.24 | 0.53 | .86 | .53 | .86 | 0.12 |
| Perfume | — | 0.3 | 0.3 | 0.3 | 0.3 | 0.3 | 0.3 |
| Gantrez ES 425 | 5.0 | 3.0 | — | — | — | — | 1.5 |
| Amphomer | — | — | 3.0 | 5.0 | 3.0 | 5.0 | — |
| FND-N-oxide (100% active) 75/20/5 | .18 | .18 | .18 | .18 | — | — | .09 |
| FND 70/25/5 (100% active) | — | — | — | — | .18 | .18 | — |
| Ethanol (SDA 40) | QS to 100 ———→ | | | | | | |

The following Examples illustrate those aspects of the present invention which utilize only the fluoroterpolymers as the hair fixing resin. The ingredients listed below in the quantities indicated were mixed together to give solutions that are useful for hair fixing.

TABLE II

| Material | % by Weight | | | |
|---|---|---|---|---|
| | Ex. 8 | Ex. 9 | Ex. 10 | Ex. 11 |
| FND-N-oxide (100% active) | — | 5.00 | — | 5.00 |
| FND (100% active) | 5.0 | — | 5.0 | — |
| Isopropanol | 4.0 | 4.0 | 4.0 | 4.0 |
| Fragrance | .30 | .30 | .30 | .30 |
| Water | 5.00 | 5.00 | 5.00 | 5.0 |
| Ethyl acetate | — | 8.80 | 8.80 | — |
| Ethanol (SDA 40) | QS to 100 ———→ | | | |

The preparations described in Examples 1 through 11 were used in the following way:

A. As a non-aersol hair spray

The hair was constrained in the desired configuration. A manually actuated pump dispensing device containing the preparation was held 10 to 12 inches from the hair. The preparation was dispensed with quick short strokes and allowed to dry.

B. As a setting lotion

To previously shampooed, towel dried hair the preparation was applied; either poured or sprayed directly onto the hair so as to saturate the hair strands. The preparation was distributed evenly throughout the hair by combing. The hair was wound onto rollers and allowed to dry. The rollers were removed and the hair was styled in the desired configuration.

C. As a styling aid to blow drying

To previously shampooed, towel dried hair the preparation was applied by spraying or pouring the finished product onto the hair so as to moisten, but not saturate, the hair fibers. A hand held blow drier was subsequently used to dry, style and set the hair in the desired configuration.

Generally, the combination of a fluoroterpolymer as described above and a secondary polymer also described above is useful as a hair fixing composition. However, as also noted above, a judicious selection of fluoroterpolymer and secondary polymer can give compositions which give a synergistic effect with regard to curl retention. We have demonstrated this by comparing the curl retention measurements of five resin systems, some of which were non-ionic in character and some of which were almost completely neutralized so that they would function as if they were non-ionic and some of which were neutralized to only a small extent so that they may be said to act as if they are ionic. The compositions prepared for this study are given in Table III below.

wire leaving a 15.24cm usable length of swatch. After tying, the hair was washed with a mild shampoo and rinsed three times with distilled water.

Each swatch was then wrapped around a Teflon roller 1.45cm in diameter in a spiral configuration. The swatches were secured to the roller by the use of two Tygon rings, one at each end of each swatch. After all the swatches were wrapped on the rollers they were left to dry overnight at room temperature.

Application of Products

The water-set curled hair swatches were removed from the Teflon rollers. The products were applied by holding the swatches, one at a time, by their root ends with one hand while holding the product dispenser vertically with the other hand parallel to the swatch at a distance of 25.4cm. Once during spraying each swatch was turned around 180° to facilitate uniform spray distribution. After the product had been applied, the swatches were laid on their sides for 30 minutes before being placed in the humidity chamber.

Test Conditions

The treated hair swatches were placed in a constant temperature (23° C)/humidity (90% RH) environment and the rate of curl relaxation was measured with time.

TABLE III

| Material | Ex. 12 | Ex. 13 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|
| Amphomer 90% neutralized with AMP | 5.0 | 5.0 | — | — | — | — | — | — | — | — |
| Resyn 28-1310 90% neutralized with AMP | — | — | 5.0 | 5.0 | — | — | — | — | — | — |
| Gantrez ES 425 (100% active) 20% neutralized with AMP | — | — | — | — | 5.0 | 5.0 | — | — | — | — |
| PVP | — | — | — | — | — | — | 5.0 | 5.0 | — | — |
| PVP/VA | — | — | — | — | — | — | — | — | 5.0 | 5.0 |
| FND-N-oxide 75/20/5 (100% active) | .175 | — | .175 | — | .175 | — | .175 | — | .175 | — |
| FND 70/25/5 (100% active) | — | .175 | — | .175 | — | .175 | — | .175 | — | .175 |
| Isopropanol | 4.0 | 4.0 | 4.0 | 4.0 | 4.0 | 4.0 | 4.0 | 4.0 | 4.0 | 4.0 |
| Fragrance | .30 | .30 | .30 | .30 | .30 | .30 | .30 | .30 | .30 | .30 |
| Water | 5.0 | 5.0 | 5.0 | 5.0 | 5.0 | 5.0 | 5.0 | 5.0 | 5.0 | 5.0 |
| Ethanol (SDA 40) | QS 100 | QS 100 | QS 100 | QS 100 | QS 100 | QS 100 | QS 100 | QS 100 | QS 100 | QS 100 |

A control sample containing all the components of the test samples excepting the fluoroterpolymer was also prepared. The quantity of fluoroterpolymer was made up in these control compositions by adding additional ethanol. In this manner, the relative relaxation rate of each test sample could be directly compared with a non-fluoroterpolymer containing control.

Curl retention ability of test compositions under conditions of high humidity were determined by the following sequence of operations:

Prewetting of the hair swatches with water, wrapping the hair swatches around rollers, drying the hair while on the rollers removing the hair from the rollers, applying the product to the curled hair swatches, placing the hair swatches (hanging freely) in the high humidity environment, recording the curl retention with time.

Preparation of samples

Hair samples used for curl retention measurements consisted of blended, untreated brown hair.

The hair swatches were prepared by tying bundles of hair weighing 1.5 to 1.8 grams with thin, insulated copper wire. The swatches were 17.78cm long and were tied at approximately 2.54cm from the root end with the Method of Measurement The measurement of curl relaxation consisted of measuring the length of curled hair swatches at different periods of time; starting from the time that the swatches are exposed to the high humidity environment (95% RH at 23° C). Length measurements were accomplished through the use of a plexiglass plate that is placed close behind the hanging hair swatches. The plexiglass plate is graduated in 0.25 inch divisions.

Using the length of the swatches at different times, curl retention can be calculated using the following formula:

$$(L_u - L_t/L_u - L_o) \times 100 = \% \text{ Curl Retention}$$

Where:

$L_u$ = length of uncurled hair swatch prior to application of product $L_o$ = curled length of the treated swatch at time $o$ $L_t$ = curled length of the treated swatch at time $t$ On the basis of these tests, it is fair to say that hair fixative preparations which contain a low quantity of replaceable or ionizable groups on the secondary resin exhibit the most synergy with non-ionic fluoroterpolymer additives. Preparations which contain a high number of replaceable or ionizable groups on the secondary resin exhibit the most synergy with ionic fluoroterpolymer additives.

The above noted synergy has also been demonstrated in another study. Curl retention tests were carried out on base compositions* containing 3% Amphomer resin (90% neutralized with AMP) or 5% Gantrez ES-425 (20% neutralized with AMP). To these base resin systems, 0.175% of fluoroterpolymer FND-N-oxide 75/20/5 or FND 70/25/5 was added. Using the resin bases without the fluoroterpolymer as standards, the effects of the ionic FND-N-oxide and the non-ionic FND on curl retention values were studies over a 24 hour period. The relative differences between the two fluoroterpolymers on curl retention values as compared to the standard are listed in Table IV below.

*base composition = isopropanol 4%; fragrance 0.3%; water 5%; 3% Amphomer (90% neutralized with AMP) or 5Gantrez ES 425 (70% neutralized with AMP); Ethanol (SDA 40% QS to 100%

TABLE IV

| | Percent Difference on Curl Retention Values at 90% RH at 23° C | | | |
|---|---|---|---|---|
| Time (Hours) | Ex. 22 3% Amphomer + .175% FND-N-oxide 75/20/5 | Ex. 23 3% Amphomer + .175% FND 70/25/5 | Ex. 24 5% Gantrez + .175% FND-N-oxide 75/20/5 | Ex. 25 5% Gantrez 425 + .175% FND 70/25/5 |
| ½ | 6.5 | 23.5 | 36.6 | 4.6 |
| 1 | 0.0 | 20.5 | 38.6 | .4 |
| 2 | 5.8 | 27.1 | 46.5 | .4 |
| 3 | −4.1 | 21.8 | 46.5 | −9.3 |
| 4 | −4.1 | 21.8 | 41.3 | −5.1 |
| 24 | −3.6 | 17.9 | 25.5 | +3.6 |

As noted above, the compositions of the present invention may be formulated as aerosol compositions. Table V below gives several typical compositions of this character.

TABLE V

| Material | Ex. 26 | Ex. 27 | Ex. 28 | Ex. 29 |
|---|---|---|---|---|
| Resyn 28-1310 | 1.00 | — | — | — |
| Amphomer | — | 1.00 | — | — |
| Gantrez ES-425 | — | — | 1.25 | — |
| Gantrez ES-225 | — | — | — | 2.00 |
| AMP | 0.18 | 0.18 | 0.10 | .08 |
| FND-N-oxide 75/20/5 | — | — | 0.15 | 0.10 |
| FND 70/25/5 | 0.20 | 0.20 | — | — |
| Perfume | 0.30 | 0.30 | 0.30 | 0.15 |
| Ethanol | 48.32 | 48.32 | 48.20 | 27.67 |
| Freon 11/12 (50/50) | 50.00 | 50.00 | 50.00 | 70.00 |

What is claimed is:

1. A process for fixing hair which comprises applying thereto an effective amount of a hair fixing composition comprising a vehicle containing an effective hair fixing amount of at least one fluoroterpolymer; said fluoroterpolymer having a molecular weight of the order of $10^3$ to $10^6$ consisting essentially by weight of:

a. 60 to 85% of at least one ester of the formula:

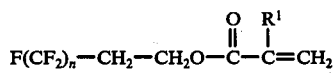

in which:

i. $n$ is a number having an average value of from 3 to 20; and
   ii. $R^1$ is hydrogen or lower alkyl having 1 to 4 carbons;

b. 10 to 30% of an ester of formula:

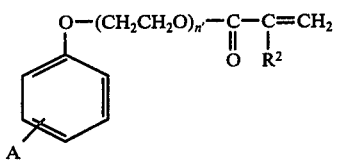

in which:

i. A is alkyl having 5 to 15 carbons;
   ii. $n'$ is a whole number having an average value of about from 20 to 45; and
   iii. $R^2$ is hydrogen or lower alkyl having 1 to 4 carbons;

c. 2 to 10% of an amine ester of formula:

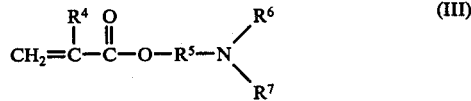

or the N-oxide or quaternary amine salt thereof in which:

i. $R^4$ is hydrogen or lower alkyl having 1 to 4 carbons;
   ii. $R^5$ is a divalent straight chain or branched chain aliphatic hydrocarbon radical having 1 to 6 carbons; and
   iii. $R^6$ and $R^7$ are lower alkyl having 1 to 4 carbons.

2. A process according to claim 1 in which the fluoroterpolymer is present in the range of from about 0.01% to 10% by weight based on the total weight of the composition.

3. A process according to claim 1 in which said hair fixing composition also contains, as a second polymer, an effective hair fixing amount of a non-fluorine containing hair fixing polymer; said second polymer having a molecular weight in the range of from about 5000 to 2,000,000.

4. A process according to claim 3 in which the fluoroterpolymer is present in the composition in the range of from about 0.01% to 10% by weight and said second non-fluorine containing hair fixing polymer is present in the range from about 1% to 10% by weight.

5. A process according to claim 4 in which the fluoroterpolymer is present in the range of from about 0.01% to 2% by weight and said second non-fluorine containing polymer is present in the range of from about 2% to 5% by weight.

6. A process according to claim 4 in which the fluoroterpolymer and said second hair fixing polymer are selected so that if the fluoroterpolymer in the composition is ionic, the second polymer will be ionic or a second polymer neutralized to a low degree and if the fluoroterpolymer in the composition is non-ionic, the second polymer will be non-ionic or a second polymer that is neutralized to a high degree.

7. A process according to claim 6 in which said low degree of neutralization is in the range of from 0% to 50% and in which said high degree of neutralization is at least 51%.

8. A process according to claim 4 wherein the fluoroterpolymer employed is made up of the following monomers:

a. about 70 to 75% by weight of

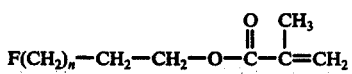

in which *n* is a number having an average value of from 5 to 15;

b. about 20 to 25% by weight of

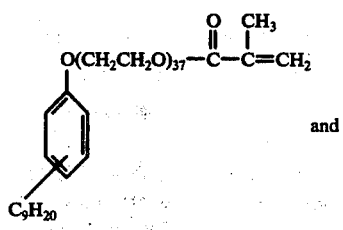

and c. about 5% by weight of

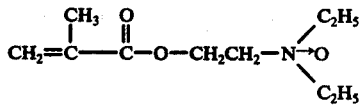

9. A process according to claim 8 in which the second polymer is a 20% neutralized monobutyl partial ester of poly(methyl vinyl ether/maleic acid) having the formula:

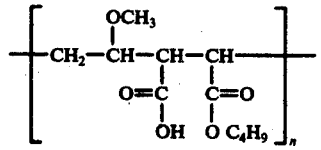

and a molecular weight of about 250,000.

10. A process according to claim 4 wherein the fluoroterpolymer employed is made up of the following monomers:

a. about 70 to 75% by weight of

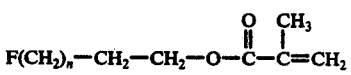

in which *n* is a number having an average value of from 5 to 15;

b. about 20 to 25% by weight of

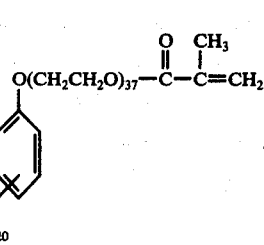

and c. about 5% by weight of

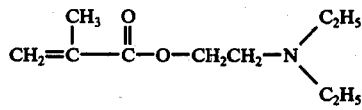

11. A hair fixing composition comprising a vehicle containing an effective hair fixing amount of a mixture containing:

A. at least one non-fluorine containing hair fixing film forming polymeric material; and
B. a fluoroterpolymer of a monomeric mixture of approximately by weight of:
   a. about 60 to 85% of at least one ester of the formula:

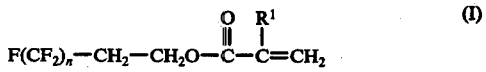

in which:
   i. n is a number having an average value of from 3 to 20; and
   ii. R¹ is hydrogen or lower alkyl having 1 to 4 carbons;
   b. about 10 to 30% of an ester of formula;

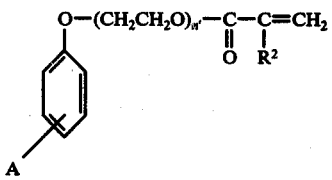

in which:
   i. A is alkyl having 5 to 15 carbons;
   ii. n' is a whole number having an average value of about from 20 to 45; and
   iii. R² is hydrogen or lower alkyl having 1 to 4 carbons;
   c. about 2 to 10% of an amine ester of the formula;

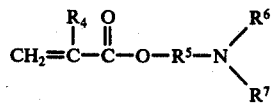

or the N-oxide or quaternary amine salt thereof in which:
   i. R⁴ is hydrogen or lower alkyl having 1 to 4 carbons;
   ii. R⁵ is a divalent straight chain or branched chain aliphatic hydrocarbon radical having 1 to 6 carbons; and iii. $R^6$ and $R^7$ are lower alkyl havng 1 to 4 carbons, said terpolymer having a molecular weight of the order of $10^3$ to $10^6$ and said film forming polymeric material having a molecular weight of about 5000 to 2,000,000.

12. A composition according to claim 11 in which the fluoroterpolymer is present in the range of from about 0.01% to 10% by weight based on the total weight of the composition, and said non-fluorine containing polymer is present in the range of from about 0.5% to 10% by weight based on the total weight of the composition.

13. A composition according to claim 12 in which said fluoroterpolymer is present in the range of from about 0.01 to 2% by weight and said non-fluorine containing polymer is present in the range of from about 2.0 to 5% by weight based on the total weight of the composition.

14. A composition according to claim 12 in which the fluoroterpolymer and said non-fluorine containing hair fixing polymer are selected so that if the fluoroterpolymer in the composition is ionic, the non-fluorine containing polymer will be ionic or a non-fluorine containing polymer neutralized to a low degree and if the fluoroterpolymer in the composition is non-ionic, the non-fluorine containing polymer will be non-ionic or a non-fluorine containing polymer that is neutralized to a high degree.

15. A composition according to claim 14 in which said low degree of neutralization is in the range of from 0% to 50% and in which said high degree of neutralization is at least 51%.

16. A composition according to claim 12 wherein the fluoroterpolymer employed is made up of the following monomers:

a. about 70 to 75% by weight of

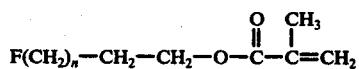

in which n is a number having an average value of from 5 to 15;

b. about 20 to 25% by weight of

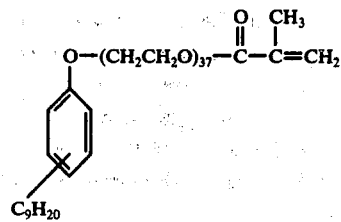

c. about 5% by weight of

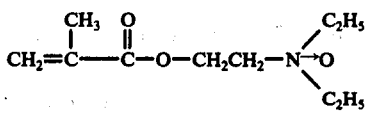

17. A composition according to claim 16 in which the non-fluorine containing polymer is a 20% neutralized monobutyl partial ester of poly(methyl vinyl ether/maleic acid) having the formula:

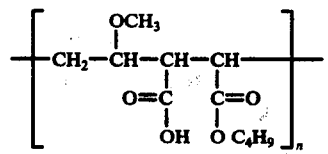

and a molecular weight of about 250,000.

18. A composition according to claim 12 wherein the fluoroterpolymer employed is made up of the following monomers:

a. about 70 to 75% by weight of

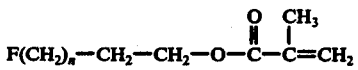

in which n is a number having an average value of from 5 to 15;

b. about 20 to 25% by weight of

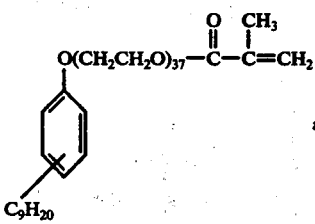

and c. about 5% by weight of

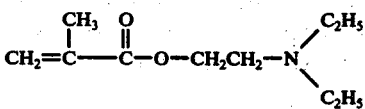

* * * * *

UNITED STATES PATENT AND TRADEMARK OFFICE
CERTIFICATE OF CORRECTION

PATENT NO. : 4,059,688
DATED : November 22, 1977
INVENTOR(S) : IRA ROSENBERG ET AL It is certified that error appears in the above-identified patent and that said Letters Patent are hereby corrected as shown below:

Column 17, lines 17 and 63; Column 19, line 55 and Column 20, line 38, please change the formula to read:

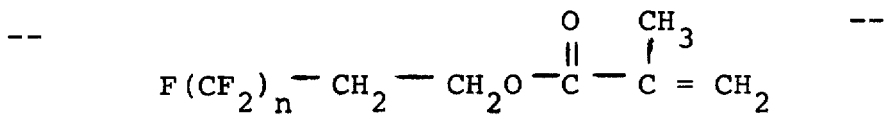

Signed and Sealed this

Thirteenth Day of February 1979

[SEAL]

Attest:

RUTH C. MASON
*Attesting Officer*

DONALD W. BANNER
*Commissioner of Patents and Trademarks*